(12) United States Patent
Farouz et al.

(10) Patent No.: US 8,314,108 B2
(45) Date of Patent: Nov. 20, 2012

(54) 5-(5-(2-(3-AMINOPROPOXY)-6-METHOXY-PHENYL)-1H-PYRAZOL-3-YLAMINO) PYRAZINE-2-CARBONITRILE, PHARMACEUTICALLY ACCEPTABLE SALTS THEREOF, OR SOLVATE OF SALTS

(75) Inventors: Francine S. Farouz, LaJolla, CA (US); Ryan Coatsworth Holcomb, Salt Lake City, UT (US); Ramesh Kasar, San Mateo, CA (US); Steven Scott Myers, Sheridan, IN (US)

(73) Assignee: Eli Lilly and Company, Indianapolis, IN (US)

( * ) Notice: Subject to any disclaimer, the term of this patent is extended or adjusted under 35 U.S.C. 154(b) by 337 days.

(21) Appl. No.: 12/634,725

(22) Filed: Dec. 10, 2009

(65) Prior Publication Data

US 2011/0144126 A1 Jun. 16, 2011

Related U.S. Application Data

(60) Provisional application No. 61/138,176, filed on Dec. 17, 2008.

(51) Int. Cl.
*A61K 31/4965* (2006.01)
(52) U.S. Cl. .................. 514/255.06; 544/336; 548/377.1
(58) Field of Classification Search ............ 514/255.06; 544/336; 548/377.1
See application file for complete search history.

(56) References Cited

FOREIGN PATENT DOCUMENTS

| WO | WO 02/070494 | 9/2002 |
|----|---|---|
| WO | WO 03/093297 | 11/2003 |
| WO | WO2004/014876 A1 | 2/2004 |
| WO | WO 2004/063198 | 7/2004 |
| WO | WO 2005/009435 | 2/2005 |
| WO | WO 2005/066163 | 7/2005 |
| WO | WO2008/117050 A1 | 10/2008 |
| WO | WO2009/089042 A1 | 7/2009 |
| WO | WO 2010/077758 | * 7/2010 |

OTHER PUBLICATIONS

Jordan, V. C. Nature Reviews: Drug Discovery, 2, 2003, 205.*
Hackam, et al. JAMA, 296(14), 2006, 1731-1732.*
Janetka, James, et a., "Checkpoint kinase inhibitors: a review of the patent literature," Expert Opinion on Therapeutic Patents, Informa Healthcare, vol. 19, No. 2, pp. 165-197 (Feb. 2009).
International Search Report and Written Opinion dated Apr. 26, 2010, in corresponding application PCT/US2009/067437.

* cited by examiner

*Primary Examiner* — Douglas M Willis
(74) *Attorney, Agent, or Firm* — Danica Hostettler

(57) ABSTRACT

The present invention provides an aminopyrazole compound, more particularly,

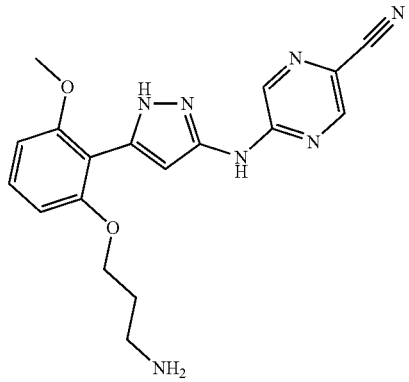

or a pharmaceutically acceptable salt thereof or a solvate of the salt, that inhibits Chk1 and is useful in the treatment of cancer.

9 Claims, No Drawings

5-(5-(2-(3-AMINOPROPOXY)-6-METHOXY-PHENYL)-1H-PYRAZOL-3-YLAMINO) PYRAZINE-2-CARBONITRILE, PHARMACEUTICALLY ACCEPTABLE SALTS THEREOF, OR SOLVATE OF SALTS

This application claims the priority of U.S. Provisional Application No. 61/138,176 filed 17 Dec. 2008.

The present invention relates to an aminopyrazole compound, or a pharmaceutically acceptable salt thereof or a solvate of the salt, that inhibits Chk1 and is useful for treating cancers characterized by defects in deoxyribonucleic acid (DNA) replication, chromosome segregation, or cell division.

Chk1 is a protein kinase that lies downstream from Atm and/or Atr in the DNA damage checkpoint signal transduction pathway. In mammalian cells, Chk1 is phosphorylated in response to agents that cause DNA damage including ionizing radiation (IR), ultraviolet (UV) light, and hydroxyurea. This phosphorylation which activates Chk1 in mammalian cells is dependent on Atr. Chk1 plays a role in the Atr dependent DNA damage checkpoint leading to arrest in S phase and at G2M. Chk1 phosphorylates and inactivates Cdc25A, the dual-specificity phosphatase that normally dephosphorylates cyclin E/Cdk2, halting progression through S-phase. Chk1 also phosphorylates and inactivates Cdc25C, the dual specificity phosphatase that dephosphorylates cyclin B/Cdc2 (also known as Cdk1) arresting cell cycle progression at the boundary of G2 and mitosis (Fernery et al., Science, 277:1495-7, 1997). In both cases, regulation of Cdk activity induces a cell cycle arrest to prevent cells from entering mitosis in the presence of DNA damage or unreplicated DNA.

Various inhibitors of Chk1 have been reported. See for example, WO 05/066163, WO 04/063198, WO 03/093297 and WO 02/070494. In addition, a series of aminopyrazole Chk1 inhibitors is disclosed in WO 05/009435.

However, there is still a need for Chk1 inhibitors that are potent inhibitors of the cell cycle checkpoints that can act effectively as potentiators of DNA damaging agents. The present invention provides a novel aminopyrazole compound, or a pharmaceutically acceptable salt thereof or solvate of the salt, that is a potent inhibitor of Chk1. The compound, or a pharmaceutically acceptable salt thereof or a solvate of the salt, potently abrogates a Chk1 mediated cell cycle arrest induced by treatment with DNA damaging agents in tissue culture and in vivo. Furthermore, the compound, or a pharmaceutically acceptable salt thereof or a solvate of the salt, of the present invention also provides inhibition of Chk2, which may be beneficial for the treatment of cancer. Additionally, the lack of inhibition of certain other protein kinases, such as CDK1, may provide a therapeutic benefit by minimizing undesired effects. Furthermore, the compound, or a pharmaceutically acceptable salt thereof or a solvate of the salt, of the present invention inhibits cell proliferation of cancer cells by a mechanism dependent on Chk1 inhibition.

The present invention provides a new aminopyrazole compound, or a pharmaceutically acceptable salt thereof or a solvate of the salt, that is an antagonist of Chk1. Such new compounds could address the need for safe and effective treatments of cancer.

The present invention provides a compound which is 5-(5-(2-(3-aminopropoxy)-6-methoxyphenyl)-1H-pyrazol-3-ylamino) pyrazine-2-carbonitrile, or a pharmaceutically acceptable salt thereof or a solvate of the salt. Preferred embodiments are 5-(5-(2-(3-aminopropoxy)-6-methoxyphenyl)-1H-pyrazol-3-ylamino) pyrazine-2-carbonitrile, 5-(5-(2-(3-aminopropoxy)-6-methoxyphenyl)-1H-pyrazol-3-ylamino) pyrazine-2-carbonitrile formic acid salt, 5-(5-(2-(3-aminopropoxy)-6-methoxyphenyl)-1H-pyrazol-3-ylamino) pyrazine-2-carbonitrile dihydrogen chloride salt and 5-(5-(2-(3-aminopropoxy)-6-methoxyphenyl)-1H-pyrazol-3-ylamino) pyrazine-2-carbonitrile methanesulfonic acid salt, and 2-pyrazinecarbonitrile, 5-[[5-[2-(3-aminopropoxy)-6-methoxyphenyl]-1H-pyrazol-3-yl]amino]monomesylate monohydrate.

As a particular embodiment, the present invention provides the compound which is 5-(5-(2-(3-aminopropoxy)-6-methoxyphenyl)-1H-pyrazol-3-ylamino)pyrazine-2-carbonitrile.

The present invention provides the formic acid, dihydrogen chloride, and methanesulfonic acid salts of 5-(5-(2-(3-aminopropoxy)-6-methoxyphenyl)-1H-pyrazol-3-ylamino) pyrazine-2-carbonitrile.

The present invention also provides the compound which is 2-pyrazinecarbonitrile, 5-[[5-[2-(3-aminopropoxy)-6-methoxyphenyl]-1H-pyrazol-3-yl]amino]monomesylate monohydrate.

The present invention provides 2-pyrazinecarbonitrile, 5-[[5-[2-(3-aminopropoxy)-6-methoxyphenyl]-1H-pyrazol-3-2-yl]amino]monomesylate monohydrate in crystalline form characterized by a X-ray powder diffraction pattern having peaks at 2θ±0.02=12.64, 21.25, and 26.15.

The present invention provides a pharmaceutical composition comprising 5-(5-(2-(3-aminopropoxy)-6-methoxyphenyl)-1H-pyrazol-3-ylamino)pyrazine-2-carbonitrile, or a pharmaceutically acceptable salt thereof or a solvate of the salt, in combination with a pharmaceutically acceptable carrier, diluent, or excipient.

The present invention provides a method of treating cancer, comprising administering to a patient in need thereof an effective amount of 5-(5-(2-(3-aminopropoxy)-6-methoxyphenyl)-1H-pyrazol-3-ylamino)pyrazine-2-carbonitrile, or a pharmaceutically acceptable salt thereof or a solvate of the salt. In addition, the present invention also provides a method of treating cancer, comprising administering to a patient in need thereof an effective amount of 5-(5-(2-(3-aminopropoxy)-6-methoxyphenyl)-1H-pyrazol-3-ylamino)pyrazine-2-carbonitrile, or a pharmaceutically acceptable salt thereof or a solvate of the salt, and ionizing radiation. Furthermore, the present invention provides a method of treating cancer, comprising administering to a patient in need thereof an effective amount of 5-(5-(2-(3-aminopropoxy)-6-methoxyphenyl)-1H-pyrazol-3-ylamino)pyrazine-2-carbonitrile, or a pharmaceutically acceptable salt thereof or a solvate of the salt, and a chemotherapy agent.

The present invention provides the use of 5-(5-(2-(3-aminopropoxy)-6-methoxyphenyl)-1H-pyrazol-3-ylamino) pyrazine-2-carbonitrile, or a pharmaceutically acceptable salt thereof or a solvate of the salt, for the manufacture of a medicament for the treatment of cancer. In addition, the present invention also provides the use of 5-(5-(2-(3-aminopropoxy)-6-methoxyphenyl)-1H-pyrazol-3-ylamino)pyrazine-2-carbonitrile, or a pharmaceutically acceptable salt thereof or a solvate of the salt, for the manufacture of a medicament for the treatment of cancer wherein said treatment comprises combination therapy with ionizing radiation. Furthermore, the present invention provides the use of 5-(5-(2-(3-aminopropoxy)-6-methoxyphenyl)-1H-pyrazol-3-ylamino)pyrazine-2-carbonitrile, or a pharmaceutically acceptable salt thereof or a solvate of the salt, for the manufacture of a medicament for the treatment of cancer by combination therapy wherein said combination therapy treatment comprises administration of said medicament and administration of one or more other chemotherapy agents to the same patient.

The present invention provides 5-(5-(2-(3-aminopropoxy)-6-methoxyphenyl)-1H-pyrazol-3-ylamino)pyrazine-2-carbonitrile, or a pharmaceutically acceptable salt thereof or a solvate of the salt, for use in therapy. The present invention also provides 5-(5-(2-(3-aminopropoxy)-6-methoxyphenyl)-1H-pyrazol-3-ylamino)pyrazine-2-carbonitrile, or a pharmaceutically acceptable salt thereof or a solvate of the salt, for use in the treatment of cancer. In addition, the present invention also provides 5-(5-(2-(3-aminopropoxy)-6-methoxyphenyl)-1H-pyrazol-3-ylamino)pyrazine-2-carbonitrile, or a pharmaceutically acceptable salt thereof or a solvate of the salt, and ionizing radiation for use in therapy. Furthermore, the present invention provides 5-(5-(2-(3-aminopropoxy)-6-methoxyphenyl)-1H-pyrazol-3-ylamino)pyrazine-2-carbonitrile, or a pharmaceutically acceptable salt thereof or a solvate of the salt, and a chemotherapy agent for use in therapy.

The present invention provides 5-(5-(2-(3-aminopropoxy)-6-methoxyphenyl)-1H-pyrazol-3-ylamino)pyrazine-2-carbonitrile, or a pharmaceutically acceptable salt thereof or a solvate of the salt, for use in the treatment of cancer. In addition, the present invention also provides 5-(5-(2-(3-aminopropoxy)-6-methoxyphenyl)-1H-pyrazol-3-ylamino)pyrazine-2-carbonitrile, or a pharmaceutically acceptable salt thereof or a solvate of the salt, and ionizing radiation for use in the treatment of cancer. Furthermore, the present invention provides 5-(5-(2-(3-aminopropoxy)-6-methoxyphenyl)-1H-pyrazol-3-ylamino)pyrazine-2-carbonitrile, or a pharmaceutically acceptable salt thereof or a solvate of the salt, and a chemotherapy agent for use in the treatment of cancer.

The present invention provides use of 5-(5-(2-(3-aminopropoxy)-6-methoxyphenyl)-1H-pyrazol-3-ylamino)pyrazine-2-carbonitrile, or a pharmaceutically acceptable salt thereof or a solvate of the salt, for the manufacture of a medicament for the treatment of cancer, wherein the medicament is to be administered simultaneously, separately or sequentially with ionizing radiation.

The present invention provides use of 5-(5-(2-(3-aminopropoxy)-6-methoxyphenyl)-1H-pyrazol-3-ylamino)pyrazine-2-carbonitrile, or a pharmaceutically acceptable salt thereof or a solvate of the salt, for the manufacture of a medicament for the treatment of cancer, wherein the medicament also comprises a chemotherapy agent or is to be administered simultaneously, separately or sequentially with a chemotherapy agent.

The present invention provides 5-(5-(2-(3-aminopropoxy)-6-methoxyphenyl)-1H-pyrazol-3-ylamino)pyrazine-2-carbonitrile, or a pharmaceutically acceptable salt thereof or a solvate of the salt, for use in simultaneous, separate or sequential combination with ionizing radiation in the treatment of cancer.

The present invention provides 5-(5-(2-(3-aminopropoxy)-6-methoxyphenyl)-1H-pyrazol-3-ylamino)pyrazine-2-carbonitrile, or a pharmaceutically acceptable salt thereof or a solvate of the salt, for use in simultaneous, separate or sequential combination with a chemotherapy agent in the treatment of cancer.

The present invention provides a pharmaceutical composition comprising 5-(5-(2-(3-aminopropoxy)-6-methoxyphenyl)-1H-pyrazol-3-ylamino)pyrazine-2-carbonitrile, or a pharmaceutically acceptable salt thereof or a solvate of the salt, together with a pharmaceutically acceptable carrier and optionally other therapeutic ingredients.

Furthermore, the present invention provides preferred embodiments of the methods and uses as described herein, in which the chemotherapy agent is selected from the group consisting of 5-fluorouracil, hydroxyurea, gemcitabine, methotrexate, pemetrexed, doxorubicin, etoposide, cisplatin, and taxol. Preferred embodiments of the methods and uses described herein are cancers selected from the group consisting of bladder cancer, colon cancer, gastric cancer, liver cancer, lung cancer, mammary cancer, melanoma, ovarian cancer, pancreatic cancer, mesothelioma, renal cancer, and uterine cancer.

The compound, or a pharmaceutically acceptable salt thereof or a solvate of the salt, of the present invention may exist as tautomeric forms. When tautomeric forms exist, each form and mixtures thereof, are contemplated in the present invention.

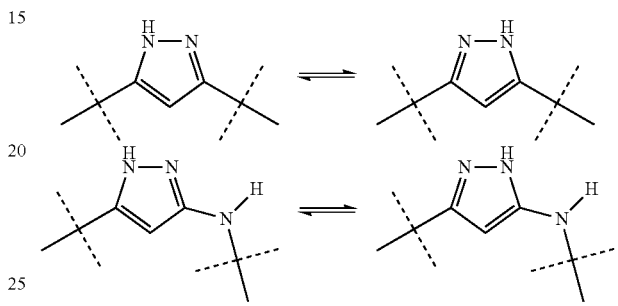

Unless otherwise defined, this invention includes pharmaceutically acceptable salts of the compound of Example 3 as well as solvates of the free base of the compound of Example 3 or a pharmaceutically acceptable salt thereof. The term "pharmaceutically acceptable salt" as used herein, refers to salts of the compound of Example 3. Examples of pharmaceutically acceptable salts and methods for their preparation are conventional in the art. See for example, Stahl et al., "Handbook of Pharmaceutical Salts: Properties, Selection and Use", VCHA/Wiley-VCH, (2002); Gould, P. L., "Salt selection for basic drugs", *International Journal of Pharmaceutics*, 33: 201-217 (1986); and Bastin et al. "Salt Selection and Optimization Procedures for Pharmaceutical New Chemical Entities", *Organic Process Research and Development*, 4: 427-435 (2000).

In addition to pharmaceutically acceptable salts, other salts are included in the invention. They may serve as intermediates in the purification of compounds or in the preparation of other pharmaceutically-acceptable salts, or are useful for identification, characterization or purification.

As used herein, the term "patient" refers to a human or nonhuman mammal More particularly, the term "patient" refers to a human.

The term "treating" (or "treat" or "treatment") refers to the process involving a slowing, interrupting, arresting, controlling, reducing, or reversing the progression or severity of a symptom, disorder, condition, or disease.

As used herein, the term "effective amount" refers to the amount or dose of the compound, or a pharmaceutically acceptable salt thereof or a solvate of the salt, of the present invention, described herein, alone or in combination with ionizing radiation or a chemotherapy agent which, upon single or multiple dose administration to the patient, provides the desired effect in the patient under diagnosis or treatment. An effective amount can be readily determined by the attending diagnostician, as one skilled in the art, by considering a number of factors such as the species of mammal; its size, age, and general health; the co-administration of other agents, if needed; the specific disease involved; the degree or severity of the disease; the response of the individual patient; the particular compound administered; the mode of administration; the bioavailability characteristics of the preparation administered; the dose regimen selected; the use of any concomitant medications; and other relevant circumstances. While not to be construed as limiting the present invention in any way, 20-150 mg/m$^2$ represents an effective amount of the compound, or a pharmaceutically acceptable salt thereof or a solvate of the salt, described herein.

As used herein, the term "combination therapy" refers to separate, simultaneous, or sequential administration of the compound, or a pharmaceutically acceptable salt thereof or a solvate of the salt, of the present invention and chemotherapy agent. Furthermore, the term "combination therapy" refers to separate, simultaneous, or sequential administration of the compound, or a pharmaceutically acceptable salt thereof or a solvate of the salt, of the present invention and ionizing radiation.

The compound of Example 3, or a pharmaceutically acceptable salt thereof or a solvate of the salt, may be formulated for administration as part of a pharmaceutical composition. As such, pharmaceutical compositions comprising the compound of Example 3, or a pharmaceutically acceptable salt thereof or a solvate of the salt, in combination with one or more pharmaceutically acceptable carriers, excipients, or diluents are an important embodiment of the invention. Examples of pharmaceutical compositions and methods for their preparation are well known in the art. See, e.g. REMINGTON: THE SCIENCE AND PRACTICE OF PHARMACY, A. Gennaro, et al., eds., 19$^{th}$ ed., Mack Publishing (1995).

The compound, or a pharmaceutically acceptable salt thereof or a solvate of the salt, of the present invention can be administered by any route which makes it bioavailable, including oral and parenteral routes. For example, the compound, or a pharmaceutically acceptable salt thereof or a solvate of the salt, can be administered orally, subcutaneously, intramuscularly, intravenously, transdermally, topically, intranasally, rectally, buccally, and the like. Alternatively, the compound, or a pharmaceutically acceptable salt thereof or a solvate of the salt, may be administered by infusion. IV infusion is the preferred route of administration.

As used herein, the following terms have the meanings indicated: "BCA" refers to bicinchoninic acid; "boc or t-boc" refers to tert-butoxycarbonyl; "BSA" refers to bovine serum albumin; "CPMS" refers to counts per minutes; "DIAD" refers to diisopropyl azodicarboxylate; "DMEM" refers to dulbecco's modified eagle's medium; "DMF" refers to dimethylformamide; "DMSO" refers to dimethylsulfoxide; "DPBS" refers to Dulbecco's phosphate-buffered saline; "DTT" refers to dithiothreitol; "EDTA" refers to ethylenediamine tetraacetic acid; "EtOH" refers to ethanol; "FBS" refers to fetal bovine serum; "HEPES" refers to N-2-hydroxyethylpiperazine-N'-2-ethanesulfonic acid; "MEM" refers to minimum essential medium; "MeOH" refers to methanol; "PBS" refers to phosphate-buffered saline; "PBST" refers to phosphate-buffered saline Tween-20, "PI" refers to propidium iodide; "RNAase" refers to ribonuclease A; "SDS" refers to sodium dodecyl sulfate; "RT" refers to room temperature; "TBS" refers to tris-buffered saline; "TBST" refers to tris-buffered saline Tween-20; "THF" refers to tetrahydrofuran; "TR-FRET" refers to time resolved fluorescent energy transfer; "Tris" refers to tris(hydroxymethyl)aminomethane; "Triton-X" refers to 4-(1,1,3,3-tetramethylbutyl)phenyl-polyethylene glycol t-octylphenoxypolyethoxyethanol polyethylene glycol tert-octylphenyl ether; and "Tween-20" refers to polysorbate 20.

The results of the following assays demonstrate evidence that the compound, or a pharmaceutically acceptable salt thereof or a solvate of the salt, of the present invention is useful as a Chk1 inhibitor, Chk2 inhibitor, and as an anticancer agent. As used herein, "IC50" refers to the concentration of an agent which produces 50% of the maximal inhibitory response possible for that agent and "EC50" refers to the concentration of an agent which produces 50% of the maximal response possible for that agent.

Chk1 Biochemical Assay

The effect of compounds on Chk1 biochemical activity can be determined using a TR-FRET assay. In this assay, a terbium-labeled antibody is used to detect phosphorylated product formed from a reaction of kinase, fluorescein-labeled substrate, and ATP. The antibody binds to the phosphorylated substrate, resulting in an increase in the TR-FRET value calculated as the ratio of acceptor signal (fluorescein) to the donor signal (terbium).

The kinase reactions (25 µL reaction volumes) are performed in 96-well half-area black polystyrene plates (Costa, cat #3694). Reactions are initiated with the addition of ATP. Final reaction conditions are 50 mM HEPES pH 7.5, 0.005% (v/v) TRITON™ X-100, 2 mM DTT, 2 mM MgCl$_2$, 104 nM fluorescein-PKC substrate (Invitrogen, cat # PV3506), 30 µM ATP, 1.5 nM active Chk1 enzyme (Millipore, cat #14-346), 4% (v/v) DMSO and serial dilution of the compound of Example 2 (1:3 serial dilution, starting at 20 µM, 10 points). Following ATP addition, the reactions are incubated at room temperature for 75 minutes, and then terminated with the addition of 25 µL of TR-FRET dilution buffer (Invitrogen #PV3574) containing 10 mM EDTA and 2.1 nM Tb-pSer antibody (Invitrogen, cat # PV3574). Quenched reactions are incubated at room temperature for 60 minutes, and then TR-FRET measured using an Envision plate reader from PerkinElmer with filters for Ex340 nm, Em495 nm and Em520 nm wavelength.

For IC50 determination, the percent inhibition for each concentration is calculated using the TR-FRET ratio from controls run on each plate. The ten-point compound concentration data are subsequently fit to a four-parameter logistic equation using ActivityBase 4.0. Absolute IC50 values are calculated from the resulting curve. The compound of Example 2 is measured in this assay to have an IC50 of <0.001 µM. This demonstrates that the compounds of the present invention are potent inhibitors of Chk1.

Chk2 Biochemical Assay

The effect of compounds on Chk2 biochemical activity can be determined using a TR-FRET assay. In this assay, a terbium-labeled antibody is used to detect phosphorylated product formed from a reaction of kinase, fluorescein-labeled substrate, and ATP. The antibody binds to the phosphorylated substrate, resulting in an increase in the TR-FRET value calculated as the ratio of acceptor signal (fluorescein) to the donor signal (terbium).

The kinase reactions (25 µL reaction volumes) are performed in 96-well half-area black polystyrene plates (Costa, cat #3694). Reactions are initiated with the addition of ATP. Final reaction conditions are 50 mM HEPES pH 7.5, 0.005% (v/v) TRITON™ X-100, 2 mM DTT, 2 mM MgCl$_2$, 104 nM fluorescein-PKC substrate (Invitrogen, cat # PV3506), 30 µM ATP, 2.5 nM active Chk2 enzyme (Millipore, cat #14-347), 4% (v/v) DMSO and serial dilution of the compound of Example 2 (1:3 serial dilution, starting at 20 µM, 10 points).

Following ATP addition, the reactions are incubated at room temperature for 75 minutes, and then terminated with the addition of 25 μL of TR-FRET dilution buffer (Invitrogen #PV3574) containing 10 mM EDTA and 2.1 nM Tb-pSer antibody (Invitrogen, cat #PV3574). Quenched reactions are incubated at room temperature for 60 minutes, and then TR-FRET measured using an Envision plate reader from PerkinElmer with filters for Ex340 nm, Em495 nm and Em520 nm wavelength.

For IC50 determination, the percent inhibition for each concentration is calculated using the TR-FRET ratio from controls run on each plate. The ten-point compound concentration data are subsequently fit to a four-parameter logistic equation using ActivityBase 4.0. Absolute IC50 values are calculated from the resulting curve. The compound of Example 2 is measured in this assay to have an IC50 of 0.0047 μM. This demonstrates that the compounds of the present invention are potent inhibitors of Chk2.

Chk1 Autophosphorylation Cell Based Assay

An inhibitor of Chk1 will prevent the kinase activity of the protein from phosphorylating substrates in cells in which the DNA damage response has been activated. An easily detectable substrate for Chk1 is an autophosphorylation site on Chk1 itself, serine 296. The following immunoblot assay can be used to measure the amount of phosphorylation of serine 296 on Chk1 and indirectly the activity level of the Chk1 protein kinase. HeLa cells (purchased from ATCC) are cultured in MEM w/Earle's salts (Invitrogen) w/L-glutamine (Gibco™) supplemented with 10% (v/v) heat inactivated FBS (Gibco™), 1×MEM non-essential amino acids (Gibco™), 1× sodium pyruvate (Gibco™) and $1 \times 10^5$ cells plated in 600 μL of MEM culture media (above) per well of a 24 well cell culture plate. Cells are incubated for 24 hours at 37° C., 5% $CO_2$ and 95%-100% humidity. Sixteen μL of a 4 μM stock of doxorubicin (Sigma) in culture media are added to each appropriate well to make a final concentration of 100 nM doxorubicin. Plates are returned to the incubator for 24 additional hours prior to Chk1 inhibitor compound addition. Compounds are solublized at 10 mM in 100% DMSO, then diluted to 2 mM in 40% (v/v) DMSO and then diluted to 100 μM with culture media plus 4% (v/v) DMSO. Subsequently serial dilutions of the compounds (1:3) are prepared over a 100 μM to 0.005 μM range. Sixty-six μL of compound stock is added to the appropriate wells in the plate to produce a final DMSO concentration of 0.4% (v/v) and a final compound concentration range between 1 μM and 0.0005 μM. The plates are returned to the incubator for an additional two hours and then removed for cell lysis and processing. The media is then removed from the plate, each well washed once with 0.5 ml of ice cold DPBS (Gibco™), all liquid removed and the plate is placed on ice for the remainder of the procedure. To each well is added 75 μL of ice cold lysis buffer, consisting of Cell Extraction Buffer (Invitrogen) containing phosphatase inhibitors (Sigma) and protease inhibitors (Roche Diagnostics). After 10 minutes each well is scraped and the lysate transferred into a 1.5 mL polypropylene microcentrifuge tube on ice. Each lysate is sonicated for 45 seconds with a plate cuphorn sonicator (Misonix) while suspended in a water/ice bath. Fifty μL of each sample is transferred into a 0.5 mL polypropylene microcentrifuge tube containing 25 μL of 4× Laemmli Sample Buffer (240 mM Tris-HCl, pH6.8, 40% glycerol, 0.05% bromophenol blue, 8% w/v SDS and 20% (v/v) beta-mercaptol ethanol), heated at 95° C. for 5 minutes and stored frozen at −80° C. The remaining lysate is used for determination of protein concentration (BCA™ protein assay kit, Thermo Scientific). Five μg of each cell lysate in sample buffer is applied to an E-Page 96 well gel (Invitrogen) and subjected to electrophoresis according to the manufacturer's instructions. Proteins are electrotransferred from the gel to Immobilon-P membrane (Millipore) according to procedures well understood in the art [Towbin et al., 1979]. The membrane is rinsed briefly with 10 mM Tris/HCl pH 8.0, 150 mM NaCl and 0.05% (v/v) Tween 20 (TBST) and soaked for one hour at 25° C. in TBST/5% (v/v) reconstituted Carnation® instant milk. The membrane is washed four times with TBST for five minutes, then soaked at 4° C. for 24 hours in TBST/5% (w/v) BSA with an appropriate dilution of rabbit anti-phosphoChk1 (serine 296) (Cell Signaling). The membrane is washed four times with TBST for five minutes at 25° C. and then soaked at 25° C. for two hours in TBST/5% milk containing an appropriate dilution of donkey anti-rabbit IgG conjugated to horseradish peroxidase (HRP; Amersham) to detect autophosphorylated Chk1 protein. The membrane is washed again four times with TBST for five minutes at 25° C. Antigen-antibody-reporter conjugates immobilized on the membrane are detected with the Super Signal Western Femto HRP-detection reagent (Pierce) as recommended by the manufacturer using a chemiluminescent imager (Fujifilm). Phospho-Chk1 (ser296) band intensities are calculated using "Total Lab" software (Nonlinear Dynamics). The percent inhibition of the doxorubicin induced Chk1 autophosphorylation is calculated by using the following formula: % inhibition=(sample phosphoChk1 band intensity−no doxorubicin negative control phosphoChk1 band intensity)/(doxorubicin positive control phosphoChk1 band intensity−no doxorubicin negative control phosphoChk1 band intensity)×100. The compound of Example 2 is measured in this assay to have an EC50 of <0.0005 μM. This demonstrates that the compounds of the present invention are potent inhibitors of Chk1.

Doxorubicin-Induced G2M Checkpoint Abrogation HeLa Cell-Based Acumen Assay

An inhibitor of Chk1 will disable the G2M DNA damage checkpoint in p53-minus tumor cells treated with the topoisomerase II inhibitor, doxorubicin. A measurement of G2M checkpoint abrogation is the phosphorylation of histone H3 on serine 10 that occurs after cells traverse the G2M checkpoint and enter mitosis. The following high content imaging assay can be used to measure the phosphorylation of histone H3 in cells. HeLa cells (purchased from ATCC) are cultured in MEM Media (Gibco™) supplemented with 10% (v/v) FBS and plated at 2000 cells per well in poly D-lysine coated clear bottom black plates (BD Biocoat Cat #3504640), 100 μL volume per well. Plates are then incubated in a cell culture incubator for 18-24 hours (37° C., 5% $CO_2$ and 95% relative humidity). Following the initial incubation, 20 μL of Gibco™ MEM Media 10% FBS containing 625 nM doxorubicin are added to the appropriate wells of the plates resulting in a final concentration of 125 nM. The plates are returned to the incubator for 24 hours, sufficient to arrest the cells at the G2M checkpoint. The next day the cells are treated with the compound of Example 2. The compound of Example 2 is solublized at 10 mM in 100% DMSO and then diluted to a 10× stock starting at 50 μM in 4% (v/v) DMSO-MEM. Subsequently serial dilutions of the compound (1:2) are prepared over a 50 μM to 0.39 μM range. Thirteen μL of compound stock is added to the appropriate wells in the plate to produce a final DMSO concentration of 0.4% and a final compound concentration range between 5 μM and 0.039 μM. The plates are returned to the incubator for an additional seven hours and then removed for fixation. Liquid is carefully removed from each well and 100 μL of PREFER™ fixative (Anatech LTD. Cat #414) is added. Plates are retained at room temperature for 20 minutes, the fixative removed, and the cells are then permeabilized by the addition of 100 μL/well of 0.1% (v/v) Triton® X 100 (Pierce Cat #28314) in DPBS (Gibco™ cat #14040) for 10 minutes. The solution is removed and the plate washed twice with 100 μL DPBS per well followed by the addition of 100 μL of DPBS containing 50 μg/mL RNAase (Ribonuclease A, Sigma Cat # R-6513) for one hour at room temperature. The RNAase solution is removed and the cells stained for the presence of histone H3 phosphorylated on serine 10 (pHH3) by adding to each well 50 μL of RNAase solution containing a 1:500 dilution of rabbit anti-pHH3 (ser10) (UBI Cat #06-570) plus 1% (w/v) BSA (Gibco™ cat #15260). Plates are sealed and kept at 4° C. overnight. The primary antibody is removed by washing each plate twice with 100 μL DPBS per well and replaced with 50 μL of a 1:750 dilution of goat anti-rabbit IgG coupled to Alexa dye 488 (Invitrogen cat #A11008) in DPBS plus 1% (w/v) BSA. Plates are kept for one hour at room temperature covered with aluminum foil to protect from light. The plates are again washed twice with 100 μL per well DPBS and replaced with 100 μL of 15 nM propidium iodide (1:100 dilution with PBS from the original solution, Molecular Probes cat #P3566). The plates are sealed with a black seal to protect the plates from light. Plates are incubated for 30 minutes to stain nuclei. Plates are scanned with ACUMEN EXPLORER™ Laser-scanning fluorescence microplate cytometers using 488 nm excitation (TTP LABTECH LTC) to measure pHH3 and DNA content including 2N, and 4N. The pHH3 positive cells are identified by mean intensity at 519 nm from Alexa 488. Total intensity at 655-705 nm from propidium iodide/DNA is used to identify individual cells and subpopulations in cell cycle (2N cells, 4N cells). The final readout for each population is determined by normalizing to the % of total cells producing a final assay output of % pHH3, %2N and %4N. 100% activity is then determined by treating cells with the maximum concentration of an inhibitor control compound at 100 nM to determine the final % activity of each compound. 0% activity is based on no compound treatment. The Relative EC50 is determined by using ACTIVITY BASE™, excel fit, curve fitting using a four parameter logistic fit, equation 205, to determine the % pHH3 relative to control max at 100%. The compound of Example 2 is measured in this assay to have an EC50 of 0.0105 μM. This demonstrates that the compounds of the present invention will disable the G2M DNA damage checkpoint.

$EC_{tfs}$ (Two-Fold Sensitization) Assay

An inhibitor of Chk1 can potentiate the anti-proliferative activity of gemcitabine (or other cytotoxics) through abrogation of the intra-S phase checkpoint, resulting in sustained and increased DNA damage. The capacity for continued tumor cell proliferation after DNA damage can be analyzed by determining the ability of cells to replicate their DNA. This assay assesses the ability of cells to replicate their DNA after cells have had an opportunity to repair DNA damage. In this assay, cells are treated with gemcitabine, and then with the compound of Example 2. Following a recovery period, cells are assayed for the ability to incorporate radioactive thymidine into DNA during S phase. The $EC_{tfs}$ parameter is a measure of the concentration of a Chk1 inhibitor necessary to reduce by half the GI90 concentration of gemcitabine, measured in this assay in the absence of Chk1 inhibition. HT-29 cells (obtained from ATCC), are grown in RPMI 1640 plus (Gibco™) 10% (v/v) heat inactivated FBS. These cells are plated at $1.3 \times 10^3$ per well on Corning Costar 96-well tissue culture plates. After plating the cells, the tissue culture plates are held at room temperature for 45 minutes, before returning to 37° C. Plates are incubated for 24 hours prior to gemcitabine addition. Before gemcitabine addition, medium is removed from all wells and replaced with 150 μL per well of fresh RPMI medium. Gemcitabine stocks at 10 mM are prepared in phosphate-buffered saline. Gemcitabine dilutions were prepared at 4× concentrations in RPMI medium and added to wells at 50 μL per well. The highest final concentration of gemcitabine used is 80 μM and dilutions proceed by four-fold steps. Two hours later, gemcitabine-containing medium is removed from the wells and replaced with 150 μL per well of fresh RPMI medium. The compound of Example 2 (10 mM in DMSO) is diluted first in DMSO to 2000× final concentrations, and then diluted 1:500 into RPMI medium to generate 4× stocks for addition to wells. The volume of addition is 50 μL. Compound dilutions proceed by two-fold steps, starting at 5000 nM. Twenty-four hours after addition of the compound of Example 2, the medium containing inhibitors is removed by aspiration and replaced with 200 μL per well of fresh RPMI medium. Seventy-two hours after removal of the compound of Example 2, tritiated thymidine labeling is initiated. $^3$H-thymidine (NET 027X001, PerkinElmer, specific activity 20 Ci/mmol) is diluted 1:20 in complete RPMI to yield a concentration of 0.05 mCi/mL. 20 μL of this solution is added to each well, yielding 1 μCi/well of $^3$H-thymidine. Cells are labeled for twenty-two hours. The medium containing $^3$H-thymidine is thoroughly removed from the wells. The plates are then frozen at −20° C., for several hours. To harvest the DNA containing incorporated $^3$H-thymidine, plates are thawed for several minutes, and then 120 μL per well of 0.1 N NaOH is added to each well. Each plate is then incubated at 37° C., with slow mixing on a rotator, for 10 minutes. DNA is harvested with a Filtermate 196 Harvester (PerkinElmer) and collected on 96-well Unifilter GF/C plates (PerkinElmer #6005174). The wells of the tissue culture plate on which cells had been labeled are washed with water 5×. The Unifilter plate membranes are washed with an additional 4.5 mL per well (3×1.0 mL and finally a 1.5 mL wash). The Unifilter plates are then dried at 37° C. for at least 6 hours. The bottom of each filter plate was sealed with a Backseal adhesive sheet (PerkinElmer), and the 50 μL/well of MicroScint-20 (Perkin Elmer) is added. Each plate is then sealed with a Topseal clear adhesive sheet (PerkinElmer). Plates are counted on a Topcount scintillation counter (PerkinElmer), at 1 minute per well. $^3$H-thymidine counts per minute (cpm) are exported into Prism (GraphPad) for analysis and plotting. A gemcitabine dose response is determined for each concentration of the compound of Example 2. To do this, cpm is normalized, setting 100% incorporation as the mean cpm for the compound of Example 2 concentration in the absence of gemcitabine and no incorporation (100% inhibition) as cpm=0 (no counts per minute). For plotting the data in Prism, the gemcitabine concentrations are transformed to log values, and dose-response curves are fit by non-linear regression. Neither top nor bottom fits are constrained. The $EC_{tfs}$ value is 0.3 nM. Furthermore, 3 nM of the compound of Example 2 decreases the EC50 of gemcitabine 7-fold from 37 nM to 5 nM in HT29 colon carcinoma cells. The action of the compound of Example 2 also increases the percentage of proliferation inhibition from 52 for gemcitabine to 73 for the combination. Alone, 3 nM of the compound of Example 2 has little effect on the proliferation of HT29 cells.

Chk1 In Vivo Target Inhibition Assay

Calu-6 cells (ATCC) are cultured in growth media (MEM with Earle's salts (Invitrogen) with L-glutamine (Gibco™) supplemented with 10% (v/v) heat inactivated FBS (Gibco™), 1×MEM non-essential amino acids (Gibco™), 1× sodium pyruvate (Gibco™)) and expanded. Cells are harvested and washed twice with phosphate buffered saline and $1 \times 10^6$ cells in growth media (without serum) are mixed with equal volume of BD Matrigel™ matrix (BD Bioscience, Franklin, N.J.), then injected subcutaneously into the flank of pre-irradiated (4.5 Gy) nude mice (athymic nude, from Harlan, Indianapolis, Ind.). At day 15 after implant (tumor size=150-200 mm$^3$), gemcitabine formulated fresh in saline (Hospira, Lake Forest, Ill.) daily is administered to animals by intraperitoneal route at 150 mg/kg dose. Six hours later animals are administered the compound of Example 2 formulated in molar ratio methane sulfonic acid/20% Captisol (CYDEX, Overland Park, Kans.) by intravenous route varying dose from 15 mg/kg downward. Animals are sacrificed 2 hours post Chk1 inhibitor dose, tumors harvested and immediately processed in ice cold Cell Extraction buffer (Invitrogen Cat #FNN0011) containing phosphatase inhibitors (Sigma) and protease inhibitors (Roche Diagnostics). Tumors are processed in 1.5-2.0 mL of lysis buffer in an iced 15 mL polypropylene conical tube using a motorized tissue homogenizer (Powergen 700) set to high for 15 seconds. With the sample kept on ice, the lysate is drawn four times through a 1 mL syringe with a 25 gauge needle. Next, 0.35 mL of tumor lysate is transferred into a 1.5 mL polypropylene microcentrifuge tube containing 0.15 mL of 4× Laemmli sample buffer (240 mM Tris-HCl, pH6.8, 40% glycerol, 0.05% bromophenol blue, 8% w/v SDS and 20% (v/v) beta-mercaptol ethanol). Sample is then mixed and heated for 5 minutes at 95° C. and sonicated for one minute using high power on a Misonix 3000 plate horn sonicator. Samples are then stored on ice, or stored at −80° C. for target inhibition assessment by western blot. The remaining lysate is used for determination of protein concentration (BCA™ protein assay kit, Thermo Scientific). Five μg of each tumor lysate in sample buffer is applied to E-Page 96 well gels (Invitrogen) and subjected to electrophoresis according to the manufacturer's instructions. Proteins are transferred to Nitrocellulose Protran BA83 membrane (Whatman) according to procedures well understood in the art [Towbin et al., 1979]. The membrane is then processed to measure Chk1 protein autophosphorylated on serine 296. The membrane is rinsed briefly with water, then 10 mM Tris/HCl pH 8.0, 150 mM NaCl and 0.05% (v/v) Tween 20 (TBST) and soaked for one hour at 25° C. in TBST/5% (w/v) reconstituted Carnation® instant milk. The membrane is then washed four times with TBST for five minutes. The membrane is soaked at 4° C. for 16 hours in TBST/5% (w/v) BSA in an appropriate dilution of rabbit anti-phosphoChk1 (serine 296) (Cell Signaling). Next, the membranes is washed four times with TBST for five minutes at 25° C. and then soaked at 25° C. for two hours in TBST/5% milk containing an appropriate dilution of donkey anti-rabbit IgG conjugated to horseradish peroxidase (HRP; Amersham) to detect phospho-Chk1 (ser 296). The membrane is washed again four times with TBST for five minutes at 25° C. Antigen-antibody-reporter conjugates immobilized on the membrane are detected with the Super Signal Western Femto HRP-detection reagent (Pierce) as recommended by the manufacturer.

Signals are detected and captured using the FUJI LAS-4000 imaging system. Phospho-Chk1 (ser296) band intensities are calculated using "Total Lab" software (Nonlinear Dynamics). The percent inhibition of the gemcitabine induced Chk1 autophosphorylation is calculated by using the following formula: % inhibition=(sample phosphoChk1 band intensity−average gemcitabine (Max) positive control phosphoChk1 band intensity)/(average negative control (Min) phosphoChk1 band intensity−average gemcitabine (Max) positive control phosphoChk1 band intensity)×100.

The compound of Example 2 is measured in this assay to have a Target Modulatory Effective Dose 50 (TMED50) for Chk1 autophosphorylation of 0.03 mg/kg.

Human Tumor Xenograft Models

The ability of Chk1 inhibitors to effect tumor killing can be determined in vivo using the Calu-6 lung and HT-29 colon tumor xenograft efficacy models. Calu-6 lung cancer cells (ATCC) are cultured in growth media (MEM w/Earle's salts (Invitrogen) with L-glutamine (Gibco™) supplemented with 10% (v/v) heat inactivated FBS (Gibco™), 1×MEM non-essential amino acids (Gibco™), 1× sodium pyruvate (Gibco™)) and HT-29 colon cancer cells (ATCC) are cultured in growth media, (McCoy's 5A medium (Gibco™) supplemented with 10% FBS (Gibco™)) and expanded. Cells are harvested and washed twice with phosphate buffered saline and $5×10^6$ cells (HT-29) or $1×10^6$ cells (Calu-6) in growth media (without serum) are mixed with equal volume of BD Matrigel™ matrix (BD Bioscience, Franklin, N.J.), then injected subcutaneously into the flank of nude mice (CD-1 nu/nu, from Charles River Labs, Wilmington, Mass.). At about day 16 after implant (150-200 $mm^3$), gemcitabine is formulated fresh in saline daily and administered to animals by intraperitoneal route at 60 mg/kg dose. Twenty four hours later animals are administered the compound of Example 2, formulated in molar ratio methane sulfonic acid/20% Captisol (CYDEX, Overland Park, Kans.) by intravenous route. After a day of rest, dosing is repeated for 3 more cycles (Q3Dx4 with Chk1 inhibitor offset+24 hours). Each dose group consists of nine animals. Tumor response is determined by tumor volume measurement performed twice a week during the course of treatment. Tumor growth inhibition (TGI) is calculated as the percent reduction in mean tumor size of a compound treated group from the mean tumor size of the vehicle-treated control group. The compound of Example 2 dosed alone and in combination with gemcitabine demonstrates excellent dose dependent anti-tumor activity in both the HT-29 and Calu-6 tumor xenograft models, with up to a six-fold increase in tumor growth inhibition over gemcitabine alone.

Single Agent Efficacy Dosing

The ability of Chk1 inhibitors to effect tumor killing can be determined in vivo using the Calu-6 lung xenograft efficacy model. Calu-6 lung cancer cells (ATCC) are cultured as described above. Cells are harvested and washed twice with phosphate buffered saline and $1×10^6$ cells (Calu-6) in growth media (without serum) are mixed with equal volume of BD Matrigel™ matrix (BD Bioscience, Franklin, N.J.), then injected subcutaneously into the flank of nude mice (CD-1 nu/nu, from Charles River Labs, Wilmington, Mass.). At about day 16 after implant (150-200 $mm^3$), the compound of Example 2 is dosed at 15 mg/kg (subcutaneously (SC), bi-daily (BID×5 rest 2 days)×3 cycles. Tumor response is determined by tumor volume measurement performed twice a week during the course of treatment. The compound of Example 2 dosed on the 5 day BID schedule (15 mg/kg) provides superior growth inhibition to the gemcitabine plus the compound of Example 2 combination schedule previously described. Complete tumor regression is rapid and durable.

Monolayer Proliferation and Cytotoxicity Assay

One measure of potency of a Chk1 inhibitor is its ability to inhibit the proliferation of cancer cells in culture due to uncontrolled replication origin activation. (Conti et al. *Cell Cycle* 6: 2760-2767, 2007) Determination of Chk1 inhibitor antiproliferative activity in cell lines derived from a broad range of tumor types is indicative of which tumor types may be clinically responsive to chemotherapy with Chk1 inhibitors. The following described cellular proliferation assay is run at Oncotest, GmbH in Germany. Thirty solid tumor cell lines are derived from 13 different tumor histotypes, each represented by 1 to 6 different cell lines (Oncotest, GmbH). They are established from cancer of the bladder, brain, colon, stomach, liver, lung, breast, ovary, pancreas, kidney and the uteri body, as well as from melanoma and pleuramesothelioma. All cell lines are established at Oncotest from patient-derived tumor xenografts (Roth et al. 1999). The origin of the donor xenografts is described by Fiebig et al. (Fieberg et al. 1992 and 1999). Cell lines are routinely passaged once or twice weekly and maintained in culture for up to 20 passages. All cells are grown at 37° C. in a humidified atmosphere with 5% $CO_2$ in RPMI 1640 medium (PAA, Cölbe, Germany) supplemented with 10% (v/v) fetal calf serum (PAA, Cölbe, Germany) and 0.1 mg/mL gentamicin (PAA, Cölbe, Germany). A modified propidium iodide assay is used to assess the cytotoxic activity of compounds against these cell lines. Briefly, adherent cells are harvested from exponential phase cultures by trypsinization, counted and plated in 96 well flat-bottomed microtiter plates at a cell density depending on the cell line (4.000-20.000 cells/well). After a 24 hour recovery period to allow the cells to adhere and to resume exponential growth, 10 µL of culture medium (6 control wells/plate) or of culture medium containing the compound of Example 2 is added. Stock solutions of the compound of Example 2 are prepared in DMSO at a concentration of 1 mM. Subsequent dilutions are done with complete RPMI 1640 cell culture medium as follows: the DMSO stock solution is first diluted 1:22 (containing 4.5% (v/v) DMSO). Using this solution, serial dilutions (half-log or 2-fold) in cell culture medium are made. For the final dilution step (1:15), 10 µL/well of the respective final compound solution is directly added to 140 µL/well culture medium. The final DMSO concentration is ≦0.3% (v/v). The compound of Example 2 is applied in triplicates in a ten point concentration curve and treatment continued for 4 days. After 4 days of treatment, the culture medium is removed and replaced by 200 µL of an aqueous 7 µg/mL PI solution. To measure the number of vital cells, cells are permeabilized by freezing, resulting in the death of all cells that had remained attached to the well after the treatment with compound. Finally, PI fluorescence is measured using the Cytofluor 4000 microplate reader (excitation λ=530 nm, emission λ=620 nm) to determine the total viable cell number. Growth inhibition is expressed as Test/Control×100 (% T/C) values. Based on the T/C values, relative IC50 values are determined using non-linear regression (log [conc. of inhibitor] versus response (% T/C)). The compound of Example 2 inhibits the growth of the majority of these tumor cell lines with an EC50 under 20 nM, suggesting the potential of broad anti-cancer activity as a single agent.

The following Preparations and Examples are provided to illustrate the invention in further detail and represent typical syntheses of the compound, or a pharmaceutically acceptable salt thereof or a solvate of the salt. The names of the compounds of the present invention are generally provided by ChemDraw Ultra® 10.0 or 11.0, except where otherwise indicated.

ROUTE A

Preparation 1

5-Isothiocyanatopyrazine-2-carbonitrile

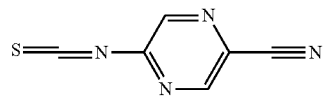

A solution of thiophosgene (1.86 g, 15 mmol) in THF (4 mL) is added dropwise to a solution of 5-aminopyrazine-2-carbonitrile (1.20 g, 10 mmol) and pyridine (2 mL) in $CH_2Cl_2$ (200 mL) and THF (25 mL) at room temperature. The reaction mixture is stirred at room temperature for 3 h. The mixture is concentrated and the crude product is diluted with ethyl acetate, filtered and concentrated to give the title compound.

Preparation 2

(tert-Butyl 3-(2-acetyl-3-methoxyphenoxy)propylcarbamate

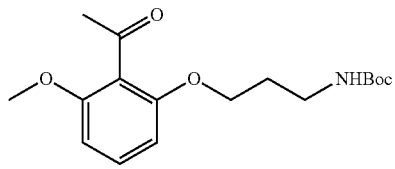

Diisopropyl azodicarboxylate (2.82 g, 14.0 mmol) is added to a stirred solution of tert-butyl 3-hydroxypropylcarbamate (2.45 g, 14.0 mmol), 1-(2-hydroxy-6-methoxyphenyl)ethanone (1.94 g, 11.7 mmol) and triphenylphosphine (3.66 g, 14.0 mmol) in THF (50 mL) at room temperature. After stirring for 18 h, the solvent is removed under reduced pressure and the crude product is chromatographed (hexane-ethyl acetate: 0-60% gradient) to afford 1.60 g of the title compound.

EXAMPLE 1

5-(5-(2-(3-Aminopropoxy)-6-methoxyphenyl)-1H-pyrazol-3-ylamino)pyrazine-2-carbonitrile formic acid salt

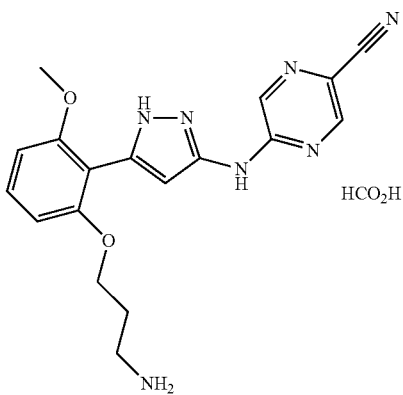

A 1 M solution of lithium hexamethyl disilazane in THF (7.6 mL, 7.6 mmol) is added slowly to a stirred solution of tert-butyl 3-(2-acetyl-3-methoxyphenoxy)propylcarbamate (1.08 g, 3.17 mmol) in dry THF (25 mL) at room temperature. After stirring for 10 min, 5-isothiocyanatopyrazine-2-carbonitrile (0.510 g, 3.17 mmol) in THF (4 mL) is added and stirring is continued for 30 min. The reaction mixture is concentrated, and redissolved in ethanol (50 mL) and acetic acid (5 mL), followed by addition of hydrazine hydrate (2 mL). The resulting reaction mixture was then heated to 120° C. for 2 min. The reaction mixture is then cooled to room temperature, diluted with water (100 mL), and extracted with ethyl acetate (2×100 mL). The organic portion is dried over anhydrous $Na_2SO_4$, filtered, and concentrated. The crude product is redissolved in dichloromethane (50 mL) and treated with trifluoroacetic acid (10 mL) and stirred at room temp for 15 min. The solvent is removed and the crude product (1.20 g) is purified using preparative HPLC to afford 0.046 g of the title compound. LC-ES/MS m/z 366.1 $[M+H]^+$.

ROUTE B

Preparation 3

1-[2-Methoxy-6-(4-methoxybenzyloxy)phenyl]ethanone

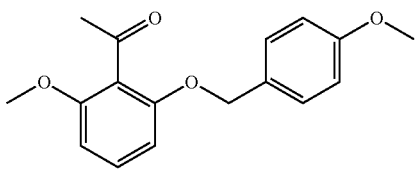

A flask is charged with 1-(2-hydroxy-6-methoxyphenyl)ethanone (30 g, 180.5 mmol), potassium carbonate, (49.9 g, 361 mmol), sodium iodide (2.68 g, 18.1 mmol), and 4-methoxybenzylchloride (27.0 mL, 198.6 mmol) in THF and the mixture is heated to reflux overnight. The mixture is cooled to room temperature, diluted with water and extracted with ethyl acetate. The combined organic extracts are washed with brine and dried over anhydrous MgSO$_4$, filtered, and concentrated. The crude product is purified by silica gel chromatography with an eluent of ethyl acetate/hexanes to give 32.51 g (57%) of the desired product as a white solid.

Preparation 4

1-(2-Methoxy-6-(4-methoxybenzyloxy)phenyl)-3,3-bis(methylthio)prop-2-en-1-one

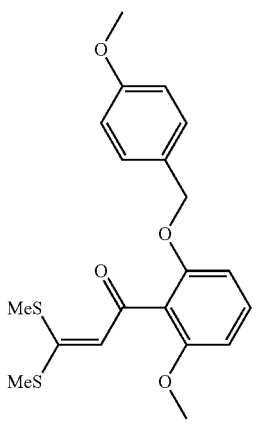

A 500 mL round bottom flask is charged with 95% NaH (7.28 g, 288 mmol) and dry DMSO is added (170 mL). To the resulting heterogeneous mixture is added dropwise, 1-[2-methoxy-6-(4-methoxybenzyloxy)phenyl]ethanone (41.2 g, 144 mmol) in dry DMSO (60 mL). The mixture is stirred at room temperature for 10 min, at which time carbon disulfide is added dropwise (8.69 mL, 144 mmol), followed immediately by methyl iodide (18.0 mL, 288 mmol). Heat and gas are evolved during the addition of both reagents prompting careful addition. The homogenous solution is stirred for 18 h at room temperature and then poured slowly into three volumes of water. The solid product is filtered and dried under high vacuum to give the title compound as an orange solid.

Preparation 5

5-Bromo-N-(5-(2-methoxy-6-(4-methoxybenzyloxy)phenyl)-1H-pyrazol-3-yl)pyrazin-2-amine

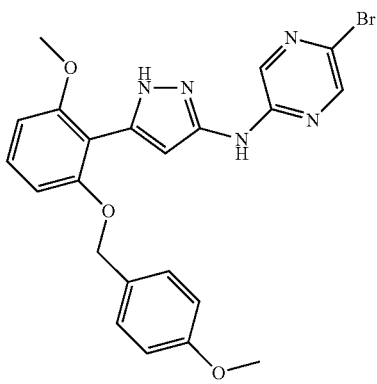

5-Bromopyrazin-2-amine (3.73 g, 21.4 mmol) is dissolved in THF (30 mL) and cooled to −78° C. A solution of n-butyllithium in hexane (10.32 mL, 23.5 mmol) is added slowly. The reaction mixture is stirred at low temperature for 15 min and then warmed slowly to room temperature and stirred an additional one hour. The mixture is recooled to 0° C. and a solution of 1-(2-methoxy-6-(4-methoxybenzyloxy)phenyl)-3,3-bis(methylthio)prop-2-en-1-one (8.39 g, 21.4 mmol) in THF (50 mL) is added via cannula. The solution becomes homogenous and is stirred 15 min at room temperature before being heated to reflux for 10 h. The solution is then cooled to room temperature and the solvent is removed under reduced pressure. The solid residue is dissolved in EtOH (150 mL) and glacial acetic acid (1.3 mL, 23.5 mmol) is added. Hydrazine hydrate (5.25 mL, 107 mmol) is added and the solution is refluxed an additional 8 h. The mixture is cooled to room temperature and concentrated under vacuum. The product is purified by silica gel chromatography (CH$_2$Cl$_2$/MeOH) to give 5.76 g (74%) of a brown solid.

Preparation 6

2-(3-(5-Bromopyrazin-2-ylamino)-1H-pyrazol-5-yl)-3-methoxyphenol

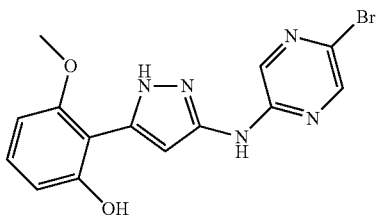

5-Bromo-N-(5-(2-methoxy-6-(4-methoxybenzyloxy)phenyl)-1H-pyrazol-3-yl)pyrazin-2-amine (3.1 g, 6.43 mmol) is dissolved in MeOH (100 mL). HCl gas is bubbled through the reaction mixture for 20 min. The mixture is stirred for 2 h and solvent is removed under reduced pressure. The residue is redissolved in 3:1 chloroform/isopropanol (100 mL) and combined with saturated NaHCO$_3$ solution (100 mL). The layers are separated and the aqueous layer is extracted with ethyl acetate (3×50 mL). The combined organic layers are concentrated and triturated with methanol to give 1.5 g (64%) of a brown solid.

Preparation 7 tert-Butyl 3-(2-(3-(5-bromopyrazin-2-ylamino)-1H-pyrazol-5-yl)-3-methoxyphenoxy)propylcarbamate

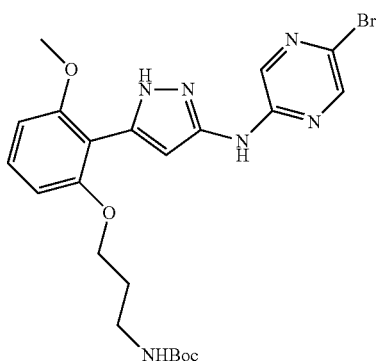

Diisopropyl azodicarboxylate (1.73 mL, 8.76 mmol) is added to a stirred solution of tert-butyl 3-hydroxypropylcarbamate (0.83 mL, 4.83 mmol), 2-(3-(5-bromopyrazin-2-ylamino)-1H-pyrazol-5-yl)-3-methoxyphenol) (1.59 g, 4.38 mmol) and polystyrene triphenylphosphine (5.91 g, 8.76 mmol) in THF (50 mL) at room temperature. After stirring for 45 min, the reaction is filtered, and the solvent is removed under reduced pressure. The resulting residue is chromatographed (methanol/CH$_2$Cl$_2$) to afford 1.27 g (54%) of a yellow solid.

Preparation 8 tert-Butyl 3-(2-(3-(5-cyanopyrazin-2-ylamino)-1H-pyrazol-5-yl)-3-methoxyphenoxy)propylcarbamate

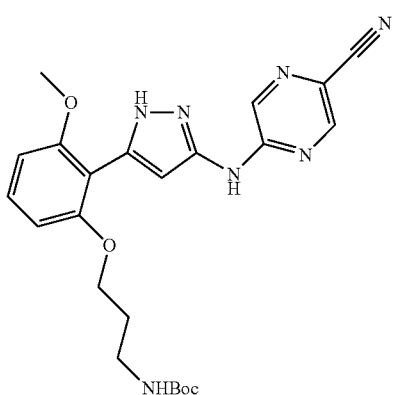

A solution of tert-butyl 3-(2-(3-(5-bromopyrazin-2-ylamino)-1H-pyrazol-5-yl)-3-methoxyphenoxy)propylcarbamate (0.378 g, 0.730 mmol) and zinc cyanide (0.10 g, 0.870 mmol) in DMF (10 mL) is degassed with a stream of nitrogen for one hour and then heated to 80° C. To the reaction is added Pd(Ph$_3$P)$_4$ (0.080 g, 0.070 mmol), and the mixture is heated overnight. The reaction is cooled to room temperature and concentrated under reduced pressure. The residue is purified by silica gel chromatography (CH$_2$Cl$_2$/MeOH) to give 0.251 g (73%) of the title compound.

ROUTE C

Preparation 9

(E)-5-(3-(2-Methoxy-6-(4-methoxybenzyloxy)phenyl)-1-(methylthio)-3-oxoprop-1-enylamino)pyrazine-2-carbonitrile

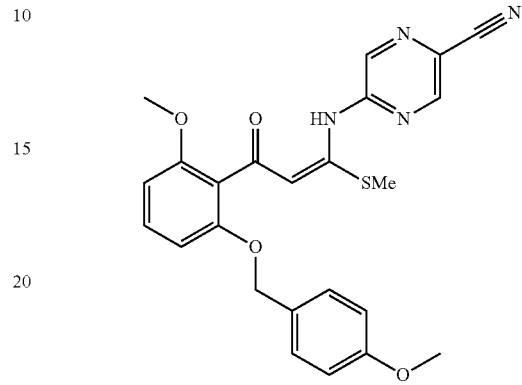

A 5 liter flange-neck flask equipped with an air stirrer rod and paddle, thermometer, water condenser and nitrogen bubbler is charged with sodium hydride (22.4 g, 560.1 mmol) and anhydrous THF (3 L). To the well stirred mixture is added 2-amino-5-cyanopyrazine (67.0 g, 557.8 mmol) portion-wise over 1.5 h while allowing for any foaming. The internal temperature remains at 22° C. throughout. The mixture is stirred for 35 min. Then 1-(2-methoxy-6-(4-methoxy-benzyloxy)-phenyl)-3,3-bis-methylsulfanyl-propenone (146.0 g, 373.9 mmol) is added at 22° C. over one hour. The yellow suspension is stirred for 45 min at room temperature and then heating is applied until the reaction is at a gentle reflux. After 19 h at 65° C. the reaction mixture is cooled to 15° C. The mixture is then split in two halves and each lot is quenched into water (2 L) and extracted with ethyl acetate (2×1 L). The organic extracts are combined and washed with brine, dried over anhydrous Na$_2$SO$_4$, filtered, and concentrated under reduced pressure at 40° C. to give 196 g of a yellow/orange solid which is used in the next step without further purification. LC-ES/MS m/z 463.2 [M+H]$^+$.

Preparation 10

5-(5-(2-Methoxy-6-(4-methoxybenzyloxy)phenyl)-1H-pyrazol-3-ylamino)pyrazine-2-carbonitrile

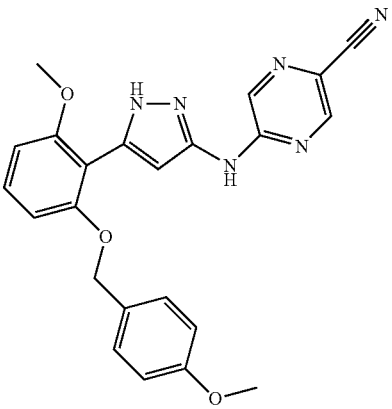

19

A 10 L flange-neck flask, equipped with an air stirrer rod and paddle, thermometer, water condenser, and nitrogen bubbler, is charged with (E)-5-(3-(2-methoxy-6-(4-methoxybenzyloxy)phenyl)-1-(methylthio)-3-oxoprop-1-enylamino)pyrazine-2-carbonitrile (196 g, 423.8 mmol) and absolute ethanol (3 L). To the stirred suspension under nitrogen is added hydrazine hydrate (41.0 mL, 838.7 mmol) and glacial acetic acid (66.0 mL, 1.15 moles). A small exotherm is noted. The yellow suspension is warmed up to 65° C. Heating is then discontinued and the reaction mixture is allowed to cool to room temperature. The mixture is allowed to stand overnight under a nitrogen atmosphere. The solid is collected by filtration, washed with fresh ethanol, and dried in vacuo at 45° C. to give 140 g (87% yield for two steps) of a bright yellow solid. The product is used in the next step without further purification. LC-ES/MS m/z 429.2 [M+H]+.

Preparation 11

5-(5-(2-Hydroxy-6-methoxyphenyl)-1H-pyrazol-3-ylamino)pyrazine-2-carbonitrile

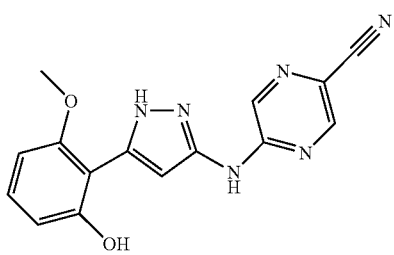

A 10 L flange-neck flask equipped with an air stirrer rod and paddle, thermometer, water condenser, and outlet to caustic solution gas scrubbers is charged with 5-(5-(2-methoxy-6-(4-methoxybenzyloxy)phenyl)-1H-pyrazol-3-ylamino)pyrazine-2-carbonitrile (140 g, 326.76 mmol) and 4 N hydrogen chloride (2500 mL, 10.0 mole) solution in 1,4-dioxane. The mixture is well stirred at 60-65° C. for 1.5 h, then the mixture is allowed to cool to 50° C. After a total of 4 h, more 4 N hydrogen chloride in 1,4-dioxane is added (1000 mL) and heating to 65° C. resumed. After one hour at this temperature the heating is stopped and the mixture allowed to cool to room temperature overnight with stirring. The mixture is filtered through a large sintered funnel The solid collected is washed with fresh 1,4-dioxane and then pulled dry briefly. The bulk filter cake is returned to the 10 L flask and vigorously stirred with water (2 L) and ethyl acetate (3.5 L). The mixture is then made alkaline by adding concentrated ammonia (440 mL). The solution is filtered and then transferred to a 5 L separatory funnel The aqueous layer is separated and extracted again with ethyl acetate (0.5 L). The combined organic layers are washed with brine, dried over sodium sulfate, filtered, and concentrated. The solid is dried in vacuo at 45° C. to give 101.3 g. The crude product is suspended in warm anhydrous tetrahydrofuran (2.2 L) and loaded onto a pad of silica (1 kg) wet packed using iso-hexane. The product is eluted with ethyl acetate. The combined fractions are partially concentrated and the resulting precipitate is collected by filtration and dried in vacuo at 40° C. overnight to give 60.9 g. LC-ES/MS m/z 309.2 [M+1]+.

20

Preparation 12 tert-Butyl 3-(2-(3-(5-cyanopyrazin-2-ylamino)-1H-pyrazol-5-yl)-3-methoxyphenoxy)propylcarbamate

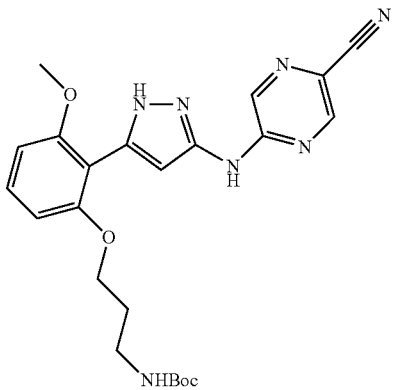

A 5 L flange-neck round-bottom flask equipped with an air stirrer rod and paddle, thermometer, pressure-equalizing dropping funnel, and nitrogen bubbler is charged with 5-(5-(2-hydroxy-6-methoxy-phenyl)-1H-pyrazol-3-ylamino)-pyrazine-2-carbonitrile (47.0 g, 152 mmol) and anhydrous THF (1.2 L). The stirred suspension, under nitrogen, is cooled to 0° C. A separate 2 L 3-necked round-bottom flask equipped with a large magnetic stirring bar, thermometer, and nitrogen bubbler is charged with triphenylphosphine (44.0 g; 168 mmol) and anhydrous THF (600 mL). The stirred solution, under nitrogen, is cooled to 0° C. and diisopropylazodicarboxylate (34.2 g; 169 mmol) is added and a milky solution is formed. After 3-4 min, a solution of t-butyl-N-(3-hydroxypropyl)-carbamate (30.3 g, 173 mmol) in anhydrous THF (100 mL) is added and the mixture is stirred for 3-4 min. This mixture is then added over 5 min to the stirred suspension of starting material at 0° C. The reaction mixture quickly becomes a dark solution and is allowed to slowly warm up to room temperature. After 6.5 h, more reagents are prepared as above using PPh3 (8 g), DIAD (6.2 g) and carbamate (5.4 g) in anhydrous THF (150 mL). The mixture is added to the reaction mixture, cooled to −5° C. and left to warm up to room temperature overnight. The solvent is removed in vacuo. The resulting viscous solution is loaded onto a pad of silica and product is eluted with ethyl acetate. The concentrated fractions are separately triturated with methanol and resulting solids are collected by filtration. The combined solids are triturated again with methanol (400 mL) and then isolated by filtration and dried in vacuo at 50° C. overnight to give 31.3 g of desired product. LC-ES/MS m/z 466.2 [M+1]+.

EXAMPLE 2

5-(5-(2-(3-Aminopropoxy)-6-methoxyphenyl)-1H-pyrazol-3-ylamino)pyrazine-2-carbonitrile dihydrogen chloride salt

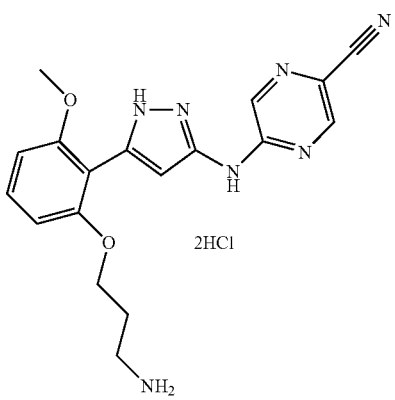

A 5 L flange-neck, round-bottom flask equipped with an air stirrer rod and paddle, thermometer, and air condenser with bubbler attached, is charged with tert-butyl 3-(2-(3-(5-cyanopyrazin-2-ylamino)-1H-pyrazol-5-yl)-3-methoxyphenoxy)propylcarbamate (30.9 g, 66.3 mmol) and ethyl acetate (3 L). The mechanically stirred yellow suspension is cooled to just below 10° C. Then hydrogen chloride from a lecture bottle is bubbled in vigorously through a gas inlet tube for 15 min with the ice-bath still in place. After 5 h the mixture is noticeably thickened in appearance. The solid is collected by filtration, washed with ethyl acetate, and then dried in vacuo at 60° C. overnight to give 30.0 g. $^1$H NMR (400 MHz, DMSO-d6) δ 2.05 (m, 2H), 2.96 (m, 2H), 3.81 (s, 3H), 4.12 (t, J=5.8 Hz, 2H), 6.08 (br s, 3H), 6.777 (d, J=8.2 Hz, 1H), 6.782 (d, J=8.2 Hz, 1H), 6.88 (br s, 1H), 7.34 (t, J=8.2 Hz, 1H), 8.09 (br s, 1H), 8.55 (br s, 1H), 8.71 (s, 1H), 10.83 (s, 1H), 12.43 (br s, 1H). LC-ES/MS m/z 366.2 [M+1]$^+$.

EXAMPLE 3

5-(5-(2-(3-Aminopropoxy)-6-methoxyphenyl)-1H-pyrazol-3-ylamino)pyrazine-2-carbonitrile

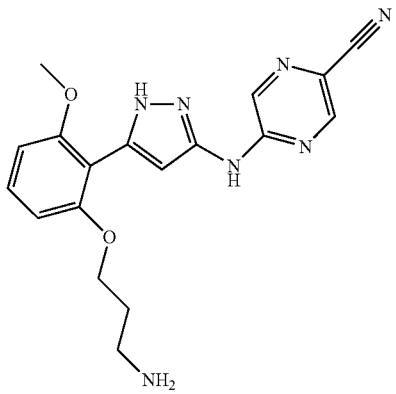

5-(5-(2-(3-Aminopropoxy)-6-methoxyphenyl)-1H-pyrazol-3-ylamino)pyrazine-2-carbonitrile dihydrogen chloride salt (3.0 g, 6.84 mmol) is suspended in 200 mL of CH$_2$Cl$_2$. 1N NaOH is added (200 mL, 200 mmol). The mixture is magnetically stirred under nitrogen at room temperature for 5 h. The solid is collected by filtration and washed thoroughly with water. The filter cake is dried in vacuo at 50° C. overnight to give 2.26 g (90%) of the free base as a yellow solid. $^1$H NMR (400 MHz, DMSO-d6) δ 1.81 (m, 2H), 2.73 (t, J=6.2 Hz, 2H), 3.82 (s, 3H), 4.09 (t, J=6.2 Hz, 2H), 6.76 (t, J=8.2 Hz, 2H), 6.93 (br s, 1H), 7.31 (t, J=8.2 Hz, 1H), 8.52 (br s, 1H), 8.67 (s, 1H). LC-MS/ES m/z 366.2 [M+1]$^+$.

EXAMPLE 4

5-(5-(2-(3-Aminopropoxy)-6-methoxyphenyl)-1H-pyrazol-3-ylamino)pyrazine-2-carbonitrile methanesulfonic acid salt

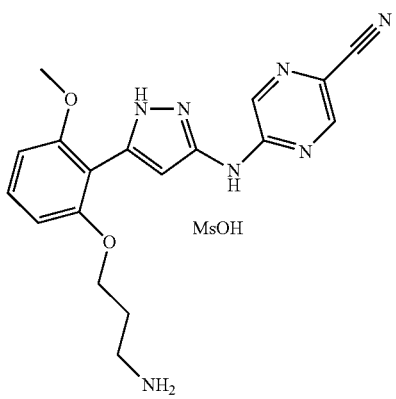

5-(5-(2-(3-aminopropoxy)-6-methoxyphenyl)-1H-pyrazol-3-ylamino)pyrazine-2-carbonitrile (1.0 g, 2.74 mmol) is suspended in MeOH (100 mL). A 1 M solution of methanesulfonic acid in MeOH (2.74 mL, 2.74 mmol) is added to the mixture dropwise with stirring. The solid nearly completely dissolves and is sonicated and stirred for 15 min, filtered, and concentrated to 50 mL. The solution is cooled overnight at −15° C. and the solid that forms is collected by filtration. The solid is dried in a vacuum oven overnight to give 0.938 g (74%) of a yellow solid. $^1$H NMR (400 MHz, DMSO-d6) δ 1.97 (m, 2H), 2.28 (s, 3H), 2.95 (m, 2H), 3.79 (s, 3H), 4.09 (t, J=5.9 Hz, 2H), 6.753 (d, J=8.4 Hz, 1H), 6.766 (d, J=8.4 Hz, 1H), 6.85 (br s, 1H), 7.33 (t, J=8.4 Hz, 1H), 7.67 (br s, 3H), 8.49 (br s, 1H), 8.64 (s, 1H), 10.70 (s, 1H), 12.31 (s, 1H). LC-ES/MS m/z 366.2 [M+1]$^+$.

ROUTE D

Preparation 13

1-[2-Methoxy-6-(4-methoxybenzyloxy)phenyl]ethanone

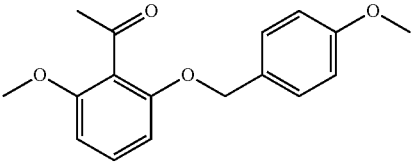

1-(2-Hydroxy-6-methoxyphenyl)ethanone (1300 g, 7.82 mol) and dimethylformamide (10.4 L) are added to a 22 L flask and stirred to obtain a solution. Potassium carbonate (2700 g, 19.54 mol) is added in portions, then stirred for at least 30 min. Using an addition funnel, 4-methoxybenzyl chloride (14700 g, 9.39 mol) is added dropwise over 2.5 h to the mixture while maintaining the temperature <30° C. The reaction mixture is warmed to 35° C. and that temperature is held for 12 h. The reaction conversion is monitored by HPLC and deemed complete after 13 h at 35° C. The slurry is filtered and the resulting solids washed with dimethylformamide (1 L). Extractive work-up of the filtrate with ethyl acetate and water, followed by concentration, provided a waxy yellow solid. To the waxy yellow solid is added methyl t-butyl ether (2.6 L). The resulting slurry is agitated. The now free flowing slurry is filtered and washed with methyl t-butyl ether (1 L). The white solid is vacuum dried yielding 1539 grams (69%) of the title compound. mp 105-107° C.

Preparation 14

1-(2-Methoxy-6-(4-methoxybenzyloxy)phenyl)-3,3-bis(methylthio)prop-2-en-1-one

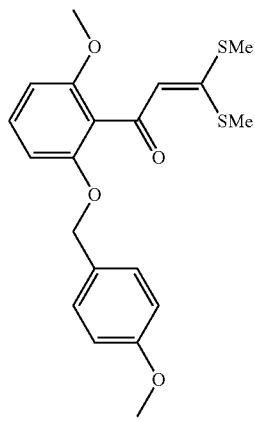

To a mixture of lithium tert-butoxide (602.4 g, 7.52 mol) in anhydrous DMSO (11.0 L) under a nitrogen atmosphere is added 1-(2-methoxy-6-(4-methoxybenzyloxy)phenyl)ethanone (1000.0 g, 3.49 mol). The resulting mixture is stirred 30 min and $CS_2$ (259 mL, 4.296 mol) is slowly added over 1 to 1.5 h while maintaining the internal temperature below 30° C. After stirring for at least one hour at ambient temperature, iodomethane (1000 g, 7.045 mol) is added slowly while maintaining the internal temperature below 30° C. The resulting mixture is stirred at ambient temperature for 30 min to one hour. Reaction completion is confirmed by HPLC. The resulting reaction mixture is cooled, followed by extractive work up with water and ethyl acetate. The resulting organic portion is concentrated to provide a slurry which is filtered and washed with ethyl acetate (1 L), followed by methyl t-butyl ether (2×1 L). The isolated solid is dried at 40° C. in a vacuum oven to provide 1057 g (77%) of the title compound. mp 93-94° C.; ES/MS m/z 391.2 $[M+1]^+$.

Preparation 15

(E)-5-(3-(2-Methoxy-6-(4-methoxybenzyloxy)phenyl)-1-(methylthio)-3-oxoprop-1-enylamino)pyrazine-2-carbonitrile

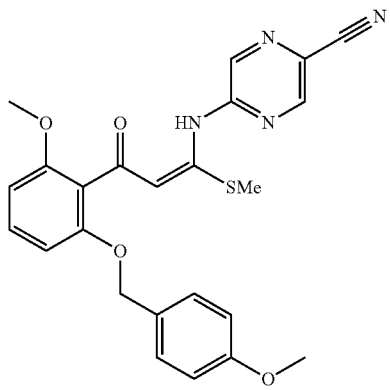

To a dry, inert 22 L flask are added sodium hydride (159.2 g, 3.98 mol) and tetrahydrofuran (10.4 L). The mixture is cooled to 5-15° C. 5-Isocyanopyrazin-2-amine (382.2 g, 3.18 mol) is added in four portions over 30 min to control the release of hydrogen, allowing foaming to subside between additions and maintaining the temperature at 10° C. The mixture is stirred for 15-90 min while allowing the temperature to increase to 15° C. To the reaction mixture is charged with 1-(2-methoxy-6-(4-methoxybenzyloxy)phenyl)-3,3-bis(methylthio)prop-2-en-1-one (1036 g, 2.65 mol) in portions to control foaming The resulting slurry is stirred for 15 min. The mixture is heated to a gentle reflux at 66° C. The reaction conversion is monitored by HPLC. The reaction mixture is quenched into chilled water (14.2 L) followed by extractive work up with ethyl acetate. The organic portion is concentrated to form a slurry which is filtered to provide 957 g (78%) of the title compound. mp 128-135° C.; ES/MS m/z 463.2 $[M+1]^+$.

Preparation 16

5-(5-(2-Methoxy-6-(4-methoxybenzyloxy)phenyl)-1H-pyrazol-3-ylamino)pyrazine-2-carbonitrile

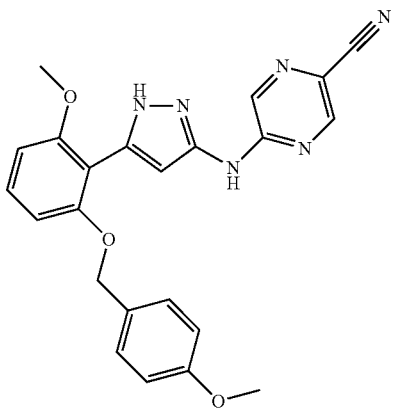

In a 20 L container are combined ethanol (11.28 L) and acetic acid (318 mL, 5.545 mol). The reaction is vented to a bleach scrubber with a nitrogen purge. (E)-5-(3-(2-Methoxy-6-(4-methoxybenzyloxy)phenyl)-1-(methylthio)-3-oxo-prop-1-enylamino)pyrazine-2-carbonitrile (940 g, 1.931 mol) and the ethanol/acetic acid solution are added to a 22 L reaction flask. To the resulting brown slurry is added hydrazine monohydrate (197 g, 3.935 mol), resulting in a slight exotherm. The resulting yellow slurry is slowly heated to 65-70° C. and monitored by HPLC. The duration of the reaction is less than one hour. The thick slurry is slowly cooled over 1-2 h to less than 30° C. The slurry is filtered and washed with cold ethanol. The material is vacuum dried at 40° C. affording (820 g, 99.1%) of the title compound. mp 215-117° C.; ES/MS m/z 429.2 $[M+1]^+$.

Preparation 17

5-(5-(2-Hydroxy-6-methoxyphenyl)-1H-pyrazol-3-ylamino)pyrazine-2-carbonitrile dihydrogen chloride salt

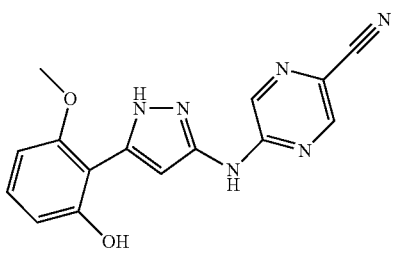

2HCl

All operations below are vented to a caustic scrubber system to control the HCl gassing. 5-(5-(2-Methoxy-6-(4-methoxybenzyloxy)phenyl)-1H-pyrazol-3-ylamino)pyrazine-2-carbonitrile (1.24 kg, 2.89 mol) and 4 N HCl in dioxane (26.06 kg, 99.28 mol) are charged to a 60 L glass reactor. The slurry is slowly heated to 60-70° C. The reaction is monitored by HPLC. After 9 h, the reaction is determined to be complete. The brown slurry is cooled to 20° C. and held overnight. The acidic reaction mixture is filtered and the cake is washed with ethyl acetate (7 L). The wet cake is vacuum dried to a constant weight to provide (1010 g, 91.84% corrected yield) of the title compound. mp 225-228° C. (free base); ES/MS m/z 309.2 $[M+1]^+$.

Preparation 18 tert-Butyl 3-(2-(3-(5-cyanopyrazin-2-ylamino)-1H-pyrazol-5-yl)-3-methoxyphenoxy)propylcarbamate

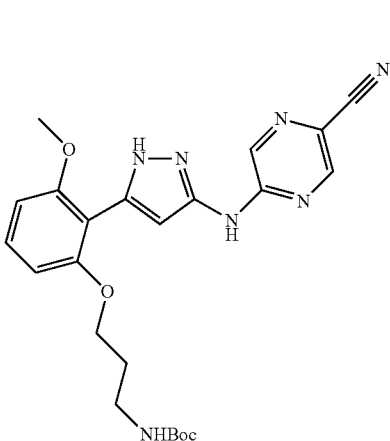

5-(5-(2-Hydroxy-6-methoxyphenyl)-1H-pyrazol-3-ylamino)pyrazine-2-carbonitrile (618 g, 1.62 mol) is slurried in tetrahydrofuran (6.18 L, 10 volumes) and chilled to −5 to 0° C. with an acetone/ice bath. Triethylamine (330 g, 3.25 mol) is added through an addition funnel over 30-40 min at −5 to 5° C. The resulting slurry is stirred at −5 to 5° C. for 60-90 min. The insoluble triethylamine hydrochloride is filtered and the solution of the phenol ((5-(2-hydroxy-6-methoxyphenyl)-1H-pyrazol-3-ylamino)pyrazine-2-carbonitrile) collected in an appropriate reaction vessel. The cake is rinsed with THF (1.24 L). The THF solution of the phenol is held at 15 to 20° C. until needed.

Triphenylphosphine (1074 g, 4.05 mol) is dissolved at room temperature in THF (4.33 L). The clear colorless solution is cooled with an acetone/ice bath to −5 to 5° C. Diisopropylazodicarboxylate (795 g, 3.89 mol) is added dropwise through an addition funnel over 40-60 min, keeping the temperature below 10° C. The resulting thick white slurry is cooled back to −5 to 0° C. tert-Butyl 3-hydroxypropylcarbamate (717 g, 4.05 moles) is dissolved in a minimum of THF (800 mL). The tert-butyl 3-hydroxypropylcarbamate/THF solution is added, through an addition funnel, over 20-30 min at −5 to 5° C. to the reagent slurry. The prepared reagent is stirred in the ice bath at −5 to 0° C. until ready for use.

The prepared reagent slurry (20%) is added to the substrate solution at 15 to 20° C. The remaining reagent is returned to the ice bath. The substrate solution is stirred at ambient for 30 min, then sampled for HPLC. A second approximately 20% portion of the reagent is added to the substrate, stirred at ambient and sampled as before. Addition of the reagent is continued with monitoring for reaction completion by HPLC. The completed reaction is concentrated and triturated with warm methanol (4.33 L, 50-60° C.) followed by cooling in an ice bath. The resulting yellow precipitate is filtered, rinsed with cold MeOH (2 L), and dried to constant weight to provide 544 g (72%) of the title compound. mp 214-216° C.; ES/MS m/z 466.2 [M+1]+.

EXAMPLE 5

2-Pyrazinecarbonitrile, 5-[[5-[2-(3-aminopropoxy)-6-methoxyphenyl]-1H-pyrazol-3-yl]amino]monomesylate monohydrate (Chemical Abstracts nomenclature)

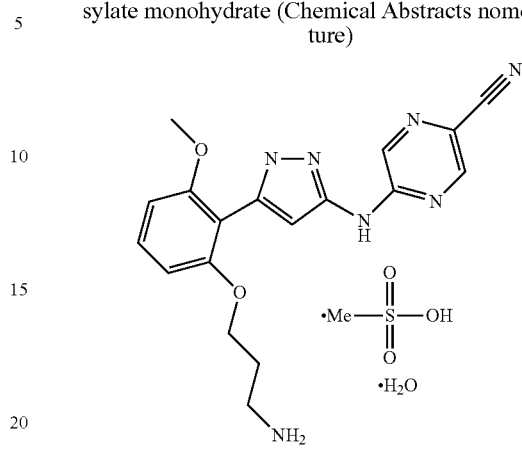

tert-Butyl 3-(2-(3-(5-cyanopyrazin-2-ylamino)-1H-pyrazol-5-yl)-3-methoxyphenoxy)propylcarbamate (1430 g, 3.07 mol) is slurried with acetone (21.5 L) in a 30 L reactor. Methanesulfonic acid (1484 g, 15.36 mol) is added through an addition funnel in a moderate stream. The slurry is warmed to reflux at about 52° C. for 1 to 3 h and monitored for reaction completion by HPLC analysis. The completed reaction is cooled from reflux to 15 to 20° C. over 4.5 h. The yellow slurry of 2-pyrazinecarbonitrile, 5-[[5-[2-(3-aminopropoxy)-6-methoxyphenyl]-1H-pyrazol-3-yl]amino]dimesylate salt is filtered, rinsed with acetone (7 L) and dried in a vacuum oven.

The dimesylate salt, (1608 g, 2.88 mol) is slurried in water (16 L). Sodium hydroxide (aqueous 50%, 228 g, 2.85 mol) is slowly poured into the slurry. The slurry is heated to 60° C. and stirred for one hour. It is then cooled to 16° C. over 4 h and filtered. The wet filter cake is rinsed with acetone (4 L) and dried to constant weight in a vacuum oven at 40° C. to provide 833 g (94%) of 2-pyrazinecarbonitrile, 5-[[5-[2-(3-aminopropoxy)-6-methoxyphenyl]-1H-pyrazol-3-yl]amino]monomesylate monohydrate. mp 222.6° C.; ES/MS m/z 366.2 [M+1]+.

EXAMPLE 5a

2-Pyrazinecarbonitrile, 5-[[5-[2-(3-aminopropoxy)-6-methoxyphenyl]-1H-pyrazol-3-yl]amino]monomesylate monohydrate (Chemical Abstracts nomenclature)

Crude 2-pyrazinecarbonitrile, 5-[[5-[2-(3-aminopropoxy)-6-methoxyphenyl]-1H-pyrazol-3-yl]amino]monomesylate monohydrate is purified using the following procedure. The technical grade 2-pyrazinecarbonitrile, 5-[[5-[2-(3-aminopropoxy)-6-methoxyphenyl]-1H-pyrazol-3-yl]amino]monomesylate monohydrate (1221 g, 2.55 mol) is slurried in a solvent mixture of 1:1 acetone/water (14.7 L). The solid is dissolved by warming the mixture to 50-55° C. The solution is polish filtrated while at 50-55° C. through a 0.22μ cartridge filter. The solution is slowly cooled to the seeding temperature of about 42-45° C. and seeded. Slow cooling is continued over the next 30-60 min to confirm nucleation. The thin slurry is cooled from 38 to 15° C. over 3 h. A vacuum distillation is set up and the acetone removed at 110-90 mm and 20-30° C. The mixture is cooled from 30 to 15° C. over 14 h, held at 15° C. for 2 h, and then filtered. The recrystallized material is rinsed with 19:1 water/acetone (2 L) and then water (6 L) and dried to constant weight in a vacuum oven at 40° C. to provide 1024 g (83.9%) of the title compound. mp 222.6° C.; ES/MS m/z 366.2 [M+1]+.

X-ray powder diffraction (XRPD) patterns may be obtained on a Bruker D8 Advance powder diffractometer, equipped with a CuKα source (λ=1.54056 angstrom) operating at 40 kV and 40 mA with a position-sensitive detector. Each sample is scanned between 4° and 35° in °2θ±0.02 using a step size of 0.026° in 2θ±0.02 and a step time of 0.3 seconds, with a 0.6 mm divergence slit and a 10.39 mm detector slit. Primary and secondary Soller slits are each at 2°; antiscattering slit is 6.17 mm; the air scatter sink is in place.

Characteristic Peak Positions and Relative Intensities:

| Peak # | °2θ   | I/Io |
|--------|-------|------|
| 1      | 8.42  | 22.8 |
| 2      | 12.64 | 85   |
| 3      | 13.16 | 36.7 |
| 4      | 16.86 | 43.7 |
| 5      | 21.05 | 44.4 |
| 6      | 21.25 | 64.3 |
| 7      | 21.63 | 42.6 |
| 8      | 24.11 | 40.6 |
| 9      | 24.69 | 30.1 |
| 10     | 25.02 | 43.1 |
| 11     | 25.4  | 30.3 |
| 12     | 26.15 | 100  |
| 13     | 29.24 | 26.2 |

Differential scanning calorimetry (DSC) analyses may be carried out on a Mettler-Toledo DSC unit (Model DSC822e). Samples are heated in closed aluminum pans with pinhole from 25 to 350° C. at 10° C./min with a nitrogen purge of 50 mL/min. Thermogravimetric analysis (TGA) may be carried out on a Mettler Toledo TGA unit (Model TGA/SDTA 851e). Samples are heated in sealed aluminum pans with a pinhole from 25 to 350° C. at 10° C./min with a nitrogen purge of 50 mL/min.

The thermal profile from DSC shows a weak, broad endotherm form 80-140° C. followed by a sharp melting endotherm at 222° C., onset (225° C., peak). A mass loss of 4% is seen by the TGA from 25-140° C.

We claim:

1. A compound which is 5-(5-(2-(3-aminopropoxy)-6-methoxyphenyl)-1H-pyrazol-3-ylamino) pyrazine-2-carbonitrile, or a pharmaceutically acceptable salt thereof or a solvate of the salt.

2. The compound according to claim 1 which is 5-(5-(2-(3-aminopropoxy)-6-methoxyphenyl)-1H-pyrazol-3-ylamino) pyrazine-2-carbonitrile, or a pharmaceutically acceptable salt thereof.

3. The compound according to claim 1 which is 5-(5-(2-(3-aminopropoxy)-6-methoxyphenyl)-1H-pyrazol-3-ylamino) pyrazine-2-carbonitrile.

4. The compound according to claim 1 which is 5-(5-(2-(3-aminopropoxy)-6-methoxyphenyl)-1H-pyrazol-3-ylamino) pyrazine-2-carbonitrile formic acid salt.

5. The compound according to claim 1 which is 5-(5-(2-(3-aminopropoxy)-6-methoxyphenyl)-1H-pyrazol-3-ylamino) pyrazine-2-carbonitrile dihydrogen chloride salt.

6. The compound according to claim 1 which is 5-(5-(2-(3-aminopropoxy)-6-methoxyphenyl)-1H-pyrazol-3-ylamino) pyrazine-2-carbonitrile methanesulfonic acid salt.

7. The compound according to claim 1 which is

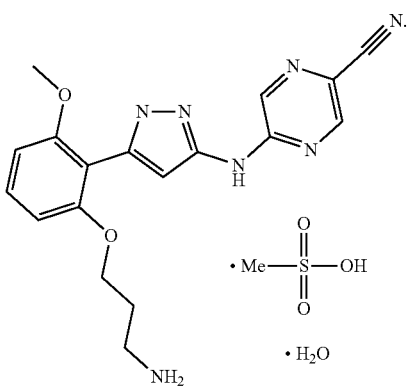

8. The compound according to claim 7 in crystalline form characterized by a X-ray powder diffraction pattern having peaks at 2θ±0.02=12.64, 21.25, and 26.15.

9. A pharmaceutical composition comprising the compound according to claim 1, in combination with a pharmaceutically acceptable carrier, diluent, or excipient.

* * * * *